United States Patent [19]

Davidson et al.

[11] Patent Number: 4,603,206

[45] Date of Patent: Jul. 29, 1986

[54] PREPARATION OF CERTAIN PYRROLO[1,2-A]IMIDAZOLES AND IMIDAZO[1,2-A]PYRIDINES

[75] Inventors: Thomas A. Davidson; Robert J. Murray, both of Penfield, N.Y.

[73] Assignee: Pennwalt Corporation, Philadelphia, Pa.

[21] Appl. No.: 674,191

[22] Filed: Nov. 23, 1984

Related U.S. Application Data

[62] Division of Ser. No. 518,514, Jul. 29, 1983, Pat. No. 4,507,481.

[51] Int. Cl.[4] .................. C07D 471/04; C07D 487/04
[52] U.S. Cl. .................................... 546/121; 548/324
[58] Field of Search ......................... 548/324; 546/121

[56] References Cited

U.S. PATENT DOCUMENTS 2,984,665  5/1961  Bortnick et al. .................... 260/251

OTHER PUBLICATIONS

MacDonald et al., J.A.C.S., vol. 81, pp. 3719–3722 (1959).
English, Jr. et al., J.A.C.S., vol. 67, pp. 2039–2041 (1945).
Arnold et al., J.A.C.S., vol. 58, pp. 1950–1952, (1936).
Seebach, Synthesis, pp. 33–34 (1969).
Grobel et al., Synthesis, pp. 360–361 (1977).
L. Werbel et al., J. Het. Chem., vol. 2, p. 287 (1965).
H. Mohrle et al., Arch. Pharmaz., 306(5), pp. 325–338 (1973).
Merck Index, 9th Edition, No. 8949 (levamisole).
Chem. Abstracts, 64, 3508h (U.S.S.R.).
Chem. Abstracts, 67, 72351w (U.S.S.R.).
Chem. Abstracts, 70, 77908e (U.S.S.R.).
Chem. Abstracts, 87, 168031f (Merck).
P. G. Gassman et al., J. Org. Chem., vol. 42, pp. 3236–3240 (1977).
P. A. Zoretic et al., J. Org. Chem., vol. 41, pp. 3587–3589 (1976).
H. Mohrle et al., Z. Naturforsch, 31b, 99–105 (1976).

*Primary Examiner*—Henry R. Jiles
*Assistant Examiner*—Bernard I. Dentz

[57] ABSTRACT

Novel 7-ether and 7-thioether derivatives of 2-aryl, 3-aryl, and 2,3-diaryl-2,5,6,7-tetrahydro-3H-pyrrolo[1,2-a]-imidazole and 8-ether and 8-thioether derivatives of 2-aryl, 3-aryl, and 2,3-diaryl-2,3,5,6,7,8-hexahydro-imidazo[1,2-a]-pyridine, such as 2,3,5,6,7,8-hexahydro-2-phenyl-8,8-dimethoxy-imidazo[1,2-a]pyridine hydrochloride, useful as immunomodulators. Diether derivatives are prepared by reacting the corresponding monothioether derivative with a positive halogenating agent in the presence of an alcohol.

2 Claims, No Drawings

PREPARATION OF CERTAIN PYRROLO[1,2-A]IMIDAZOLES AND IMIDAZO[1,2-A]PYRIDINES

This application is a division of application Ser. No. 518,514, filed July 29, 1983, now U.S. Pat. No. 4,507,481.

BACKGROUND OF THE INVENTION

This invention relates to novel 2-aryl, 3-aryl, and 2,3-diaryl-2,5,6,7-tetrahydro-3H-pyrrolo[1,2-a]imidazoles substituted in the 7-position by a substituted ether or thioether group, to novel 2-aryl, 3-aryl and 2,3-diaryl-2,3,5,6,7,8-hexahydroimidazolo[1,2-a]pyridines substituted in the 8-position by a substituted ether or thioether group, and to methods for the preparation of said imidazoles and pyridines.

The basic ring structures, 2-phenyl-2,5,6,7-tetrahydro-3H-pyrrolo-[1,2-a]imidazole and 2-phenyl-2,3,5,6,7,8-hexahydro-3H-imidazo-[1,2-a]pyridine, have been described in H. Mohrle et al, *Arc. Pharmaz.*, 306(5), 325–338 (1973); and the basic ring structures, 3-phenyl-2,5,6,7-tetrahydro-3H-pyrrolo[1,2-a]imidazole and 3-phenyl-2,3,5,6,7,8-hexahydroimidazo[1,2-a]pyridine, have been described in H. Mohrle et al, *Z. Naturforsch*, 31b, 99–105 (1976). None of the ring systems is associated with any interesting pharmacology and it is not believed that any ether or thioether derivatives have been reported.

BRIEF SUMMARY OF THE INVENTION

The present invention pertains to new 2-aryl, 3-aryl, and 2,3-diaryl-2,5,6,7-tetrahydro-7-(substituted oxo or thio)-3H-pyrrolo[1,2-a]imidazoles and 2-aryl, 3-aryl, and 2,3-diaryl-2,3,5,6,7,8-hexahydro-8-(substituted oxo or thio)-imidazo[1,2-a]pyridines, including such compounds having a double-bond at the 2,3-position, wherein the 7 position of the imidazoles and the 8 position of the pyridines are mono- or di-substituted with —$XR_1$, where X is O or S(O)n; n is 0, 1, or 2; and $R_1$ is hydrogen, lower alkyl, phenyl, benzyl, or phenyl or benzyl substituted with lower alkyl, amino, lower alkylamino, nitro, halogen (preferably chloro), hydroxy or lower alkoxy, including all stereoisomers, racemic and optically active forms, and including all pharmaceutically acceptable addition salts of these compounds. By the term "lower alkyl" as used herein is intended an alkyl group, straight or branched, containing four or less carbon atoms.

DETAILED DESCRIPTION

Utility:

The compounds of this invention have been found to modulate immunological functions in warm-blooded animals. Immunomodulators are used, for example, in the control of neoplastic diseases, infectious diseases including those of bacterial or viral origin, inflammatory and allergic reactions, autoimmune and immunodeficiency diseases.

Compounds:

Preferred compounds are those of the formula

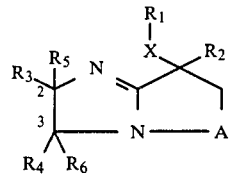

where X and $R_1$ are as defined above; $R_2$ is H or $XR_1$; A is $CH_2$ or $CH_2CH_2$; $R_3$ and $R_4$ are independently selected from H, lower alkyl, aryl (preferably phenyl), or aryl substituted with lower alkyl, amino, lower alkylamino, nitro, hydroxy, lower alkoxy or halogen (preferably chloro), provided that at least one of $R_3$ and $R_4$ is aryl or substituted aryl; and $R_5$ and $R_6$ are each hydrogen or join to form a double bond at the 2,3-position.

Formation of Compounds:

The thioether substituted amidine compounds can be prepared by the reaction of a disulfide ($R_1SSR_1$) and the corresponding 2-aryl, 3-aryl or 2,3-diaryl-2,5,6,7-tetrahydro-3H-pyrrolo[1,2-a]imidazole or 2-aryl, 3-aryl or 2,3-diaryl-2,3,5,6,7,8-hexahydro-3H-imidazo[1,2-a]pyridine substrate in the presence of a suitable base such as n-butyl lithium.

The ratios of substrate, base, and disulfide are important for high yields of the desired mono- or disulfenylated compound. In general, optimal mono-sulfenylation is obtained with one equivalent of the amidine compound to one equivalent of disulfide to two equivalents of base. Additional disulfide increases the amount of disulfenylation and reduced amounts of base also result in increased disulfenylation as well as unreacted starting material at the expense of monosulfenylated product. The preferred reactant ratios for disulfenylation are one equivalent of amidine to two equivalents of disulfide to two equivalents of base.

The temperature range for monosulfenylation can be from about −78° C. to about 0° C., preferably at or below −10° C. From 0° C. to 23° C., disulfenylation becomes prominent. In disulfenylation, the lower temperatures are still preferred, but up to about 23° C. can be tolerated.

The preferred reaction solvent is tetrahydrofuran, although ethereal solvents and hydrocarbons such as diethyl ether, dioxane, n-hexane, and toluene can also be employed. The reaction times are not critical and are dependent on the reactants, reactant ratios, temperature, and the like. Such times normally range from about 0.5 to about 2.0 hours, although up to about 12 hours should not be detrimental.

Several different bases can be used, such as n-butyl lithium, lithium diisopropyl amide and sodium amide. Butyl lithium is used in the following representative examples.

The sulfoxide compounds (wherein X is SO) can be prepared by oxidation of the corresponding thioethers (wherein X is S) with an organic peracid such as meta-chloroperbenzoic acid in methylene chloride.

The sulfone compounds (wherein X is $SO_2$) can be prepared by oxidation of the corresponding thioethers or their sulfoxide derivatives with excess potassium hydrogen persulfate in methanol according to the general procedure of B. Trost and D. Curran, *Tetrahedron Lett.*, 22, 1287 (1981).

Ether derivatives (wherein X is O) can be prepared by reaction of the thioether derivatives with an excess of a positive halogenating agent such as chloramine-T in alcohol solvent or N-bromosuccinimide in methanol-acetonitrile mixtures. The temperature employed for this reaction is not critical. It should be high enough to provide a reasonable rate but not so high as to cause decomposition. The boiling point of the reacting alcohol can conveniently be employed and can be expected to provide a reasonable rate of reaction.

The pharmaceutically acceptable acid addition salts of the substituted amidine compounds of this invention can be formed with strong or moderately strong organic or inorganic acids by methods known to the art. For example, an ethanolic solution of the amidine may be treated with inorganic acid to give the desired amine salt as a solid. Exemplary of the salts which are included in this invention are fumarate, maleate, citrate, lactate, oxalate, tartrate, hydrochloride, hydrobromide, sulfate, nitrate and phosphate salts.

The starting 2-aryl-2,5,6,7-tetrahydro-3H-pyrrolo[1,2-a]imidazoles and 2-aryl-2,3,5,6,7,8-hexahydroimidazo[1,2-a]pyridines can be prepared by the procedure of H. Mohrle et al., *Arch Pharmaz.*, 306(5), 325 (1973). The starting 3-aryl-2,5,6,7-tetrahydro-3H-pyrrolo[1,2-a]imidazoles and 3-aryl-2,3,5,6,7,8-hexahydroimidazo[1,2-a]pyridines can be prepared by the procedure of H. Mohrle et al., *Z. Naturforsch*, 31b, 99 (1976).

Alternatively, the 3-aryl and the 2,3-diaryl-2,5,6,7-tetrahydro-3H-pyrrolo-[1,2-a]imidazoles and the 3-aryl and the 2,3-diaryl-2,3,5,6,7,8-hexahydroimidazo-[1,2-a]pyridines can be prepared by reaction of cyclic methylthioimines as their acid addition salts (such as 2-methylthio-3,4,5,6-tetrahydropyridinium iodide) with 2-aryl and 2,3-diarylaziridines. The preferred reaction solvent is alcohol although polar aprotic solvents such as dimethylformamide and dimethylsulfoxide can be employed as well. Reaction temperatures of 0° C. to 150° C. are suitable for the reaction with the reflux temperature of solvent conveniently employed. The reaction times are not critical and are dependent on the reactants, temperature, and the like. Such times normally range from 1 to 3 hours, although up to 24 hours has not been found to be deterimental. The reaction has been found to behave regiospecifically such that when a 2-arylaziridine is used, only the 3-aryl amidine derivatives are formed. Furthermore, when optically active 2-phenylaziridine is employed, only racemic amidine is recovered. The starting thioimines and aziridines are generally available in the literature.

General procedures used in the following representative examples for preparation of the thioether compounds are as follows:

(A) Monosulfenylation of Amidines: n-Butyl lithium (2 equivalents) is added in the presence of nitrogen to a stirred, cold (−78° C.) solution of the amidine (1 equivalent) in dry THF (tetrahydrofuran). After 30–60 minutes, the requisite disulfide (1 equivalent), dissolved or suspended in THF, is added, and the reaction is allowed to stir for a further 1 hour at −78° C. and is then allowed to warm to −10° C. over 1.5 hours. The mixture is poured onto cold 1 normal HCl, washed with ether to remove thiol by-product and any unreacted disulfide, neutralized with saturated $NaHCO_3$ solution and extracted with solvents such as ether or toluene to give the monosulfenylated amidines, usually as oils. Treatment of an ethanolic solution of the free base with ethanolic HCl or ethanolic $H_2SO_4$ gives the desired hydrochloride or sulfate salts as solids.

(B) Disulfenylation of Amidines: The procedure for preparation of the disulfenylated amidine is the same as in General Procedure (A), except that 2 equivalents of the requisite disulfide are added. Treatment of an ethanolic solution of the free base with an inorganic acid gives the desired amine salt as a solid.

In the following examples, all temperatures are in degrees centigrade.

ILLUSTRATIVE EXAMPLES

Example 1

Preparation of 2,5,6,7-Tetrahydro-2-phenyl-7-methylthio-3H-pyrrolo[1,2-a]imidazole hydrochloride To a solution of 4.8 g (0.026 mol) of 2,5,6,7-tetrahydro-2-phenyl-3H-pyrrolo[1,2-a]imidazole in 50 ml of dry THF and stirred at −75° C. under $N_2$ was added dropwise 19.8 ml (0.052 mol) of n-BuLi (2.6M in n-hexane). The resulting dark-colored solution was stirred at −75° for 1 hr and was then treated all at once with 2.4 g (0.026 mol) of dimethyl disulfide in 10 ml of THF. After stirring at −75° for 1 hr, the reaction mixture was allowed to warm up to −10° (1½ hr), and the yellow-orange solution was then poured onto 250 ml of ice-cold 1N HCl solution. The colorless aqueous solution was washed with $Et_2O$ to remove thiol and was then neutralized with saturated $NaHCO_3$ solution. The pale yellow mixture was extracted with $Et_2O$ (3 × 1 liter); the ethereal extracts were combined on the basis of TLC and evaporated to afford 2.6 g (43.1%) of the monosulfenylated amidine free base as a tan oil. Treatment of an ethanolic solution (5 ml) of the monosulfenylated amidine with EtOH/HCl and dilution with $Et_2O$ afforded 1.35 g (19.3%) hydrochloride salt as a tan amorphous powder; m.p. 189°–190°.

Anal. Calc'd for $C_{13}H_{17}ClN_2S$: C, 58.08; H, 6.37; Cl, 13.18; N, 10.42; S, 11.92. Found: C, 57.91; H, 6.42; Cl, 13.38; N, 10.30; S, 11.35.

Example 2

Preparation of 2,5,6,7-Tetrahydro-2-phenyl-7-phenylthio-3H-pyrrolo[1,2-a]imidazole hydrochloride 2,5,6,7-Tetrahydro-2-phenyl-3H-pyrrolo[1,2-a]imidazole was reacted with 2 equivalents of n-BuLi and 1 equivalent of diphenyl disulfide according to the general procedure A above and afforded the free base as an amorphous solid in 84.6% yield. Treatment of an ethanolic solution of the free base with EtOH/HCl followed by $Et_2O$ yielded the hydrochloride salt as an amorphous colorless powder (33.7%); m.p. 202°–204°.

Anal. Calc'd for $C_{18}H_{19}ClN_2S$: C, 65.34; H, 5.78; Cl, 10.71; N, 8.46; S, 9.69. Found: C, 65.39; H, 5.84; Cl, 10.99; N, 8.46; S, 9.69.

Example 3

Preparation of 2,5,6,7-Tetrahydro-2-phenyl-7-p-methoxybenzylthio-3H-pyrrolo[1,2-a]imidazole hydrochloride 2,5,6,7-Tetrahydro-2-phenyl-3H-pyrrolo[1,2-a]imidazole was reacted with 2 equivalents of n-BuLi and 1 equivalent of p-methoxybenzyl disulfide according to the general procedure A above and afforded the free base as a dark green oil in 62% yield. Treatment of an ethanolic solution of the free base with EtOH/HCl followed by $Et_2O$ yielded the hydrochloride salt as a cream-colored amorphous powder (27.9%); m.p. 195°–197°.

Anal. Calc'd for $C_{20}H_{23}ClN_2OS$: C, 64.07; H, 6.18; Cl, 9.45; N, 7.47; O, 4.26; S, 8.55. Found: C, 64.02; H, 6.21; Cl, 9.27; N, 7.46; O, 4.47; S, 9.18.

Example 4

Preparation of 2,5,6,7-Tetrahydro-2-phenyl-7,7-di(methylthio)-3H-pyrrolo[1,2-a]imidazole perchlorate 2,5,6,7-Tetrahydro-2-phenyl-3H-pyrrolo[1,2-a]imidazole was reacted with 2 equivalents of n-BuLi and 2 equivalents of dimethyl disulfide according to the general procedure B and afforded the disulfenylated amidine free base as an oil in 69.3% yield. Treatment of an ethanolic solution of the amidine free base with $HClO_4$ yielded the solid perchlorate salt (45.8%); m.p. 181°–183°.

Anal. Calc'd for $C_{14}H_{19}ClN_2O_4S_2$: C, 44.38; H, 5.05; Cl, 9.36; N, 7.39; O, 16.89. Found: C, 44.48; H, 5.18; Cl, 9.56; N, 7.23; O, 16.85.

Example 5

Preparation of 2,5,6,7-Tetrahydro-2-phenyl-7,7-di(phenylthio)-3H-pyrrolo[1,2-a]imidazole 2,5,6,7-Tetrahydro-2-phenyl-3H-pyrrolo[1,2-a]imidazole was reacted with 2 equivalents of n-BuLi and 2 equivalents of diphenyl disulfide according to the general procedure B and afforded the disulfenylated amidine free base as a colorless solid (62.2%); m.p. 154°–156°.

Anal. Calc'd for $C_{24}H_{22}N_2S_2$: C, 71.60; H, 5.50; N, 6.95; S, 15.92. Found: C, 71.42; H, 5.67; N, 6.83; S, 15.76.

Example 6

Preparation of 2,5,6,7-Tetrahydro-2-phenyl-7-i-propylthio-3H-pyrrolo[1,2-a]imidazole hydrochloride 2,5,6,7-Tetrahydro-2-phenyl-3H-pyrrolo[1,2-a]imidazole was reacted with 2 equivalents of n-BuLi and 1 equivalent of i-propyldisulfide according to the general procedure A above and afforded the free base as a yellow oil in 79.8% yield. Treatment of an ethanolic solution of the free base with EtOH/HCl followed by $Et_2O$ yielded the hydrochloride salt as an amorphous colorless powder (9.3%); m.p. 240°–242°.

Anal. Calc'd for $C_{15}H_{21}ClN_2S$: C, 60.68; H, 7.13; Cl, 11.94; N, 9.43; S, 10.80. Found: C, 60.57; H, 7.13; Cl, 12.40; N, 9.42; S, 11.11.

Example 7

Preparation of 2,5,6,7-Tetrahydro-2-phenyl-7-n-butylthio-3H-pyrrolo[1,2-a]imidazole hydrochloride 2,5,6,7-Tetrahydro-2-phenyl-3H-pyrrolo[1,2-a]imidazole was reacted with 2 equivalents of n-BuLi and 1 equivalent of n-butyldisulfide according to the general procedure A above and afforded the free base as a dark oil in 50% yield. Treatment of an ethanolic solution of the free base with EtOH/HCl followed by $Et_2O$ yielded the hydrochloride salt as an amorphous grey solid (8.9%); m.p. 223°–225°.

Anal. Calc'd for $C_{16}H_{23}ClN_2S$: C, 61.82; H, 7.46; Cl, 11.40; N, 9.01; S, 10.31. Found: C, 61.85; H, 7.77; Cl, 11.80; N, 9.03; S, 10.57.

Example 8

Preparation of 2,5,6,7-Tetrahydro-2-p-methoxyphenyl-7-phenylthio-3H-pyrrolo[1,2-a]imidazole hydrochloride 2,5,6,7-Tetrahydro-2-p-methoxyphenyl-3H-pyrrolo[1,2-a]imidazole was reacted with 2 equivalents of n-BuLi and 1 equivalent of diphenyldisulfide according to the general procedure A above and afforded the free base as a colorless solid in 78.5% yield; m.p. 115°–119°. Treatment of an ethanolic solution of the free base with EtOH/HCl followed by $Et_2O$ yielded the hydrochloride salt as an amorphous colorless powder (20.1%); m.p. 230°–232°.

Anal. Calc'd for $C_{19}H_{21}ClN_2OS$: C, 63.23; H, 5.86; Cl, 9.82; N, 7.76; S, 8.88. Found: C, 62.48; H, 5.77; Cl, 9.94; N, 7.40; S, 8.85.

Example 9

Preparation of 2,5,6,7-Tetrahydro-2-phenyl-7-(2,6-dichlorophenylthio)-3H-pyrrolo[1,2-a]imidazole hydrochloride 2,5,6,7-Tetrahydro-2-phenyl-3H-pyrrolo[1,2-a]imidazole was reacted with 2 equivalents of n-BuLi and 1 equivalent of 2,6-dichlorophenyldisulfide according to the general procedure A above except that when the reaction mixture was poured into the aq HCl solution, the HCl salt of the desired product precipitated. It was collected, washed well with cold $H_2O$, then $Et_2O$ and dried in vacuo; yield 40.7%; m.p. 96°–99°. Neutralization of the acidic filtrate with $NaHCO_3$, followed by extraction with $Et_2O$, yielded an additional amount of the desired product as the free base (39.2%).

Anal. Calc'd. for $C_{18}H_{17}Cl_3N_2S$: C, 50.96; H, 4.30; Cl, 24.78; N, 6.48; S, 7.98. Found: C, 50.93; H, 4.66; Cl, 25.31; N, 6.60; S, 7.55.

Example 10

Preparation of 2,3,5,6,7,8-Hexahydro-2-phenyl-8-methylthioimidazo[1,2-a]pyridine hydrochloride To a solution of 10.2 g (0.051 mol) of 2,3,5,6,7,8-hexahydro-2-phenylimidazo[1,2-a]pyridine in 100 ml of dry THF and stirred at $-75°$ under $N_2$ was added dropwise 41.5 ml (0.102 mol) of n-BuLi (2.45M in n-hexane). The resulting blood-red solution was stirred at $-75°$ for 50 min and was then treated all at once with 4.8 g (0.051 mol) of dimethyl disulfide in 20 ml of dry THF. After stirring at $-75°$ for 1 hour, the reaction mixture was allowed to warm to $-10°$ ($\sim 1\frac{1}{2}$ hr) and the yellow-orange solution was then poured onto 500 ml of ice-cold 1N HCl solution. The colorless aqueous solution was washed with $Et_2O$ ($3\times 500$ ml) to remove thiol and was then neutralized with saturated $NaHCO_3$ solution. The pale yellow mixture was extracted with $Et_2O$ ($6\times 500$ ml), toluene ($4\times 500$ ml) and, finally, $CHCl_3$ ($1\times 500$ ml). The organic extracts were combined on the basis of TLC ($CHCl_3$:EtOH:$NH_4OH$(25%)40:60:2); thus, $Et_2O$ extracts 2–6 and toluene extracts 1–4 were combined, dried and evaporated to afford 6.5 g (51.7%) of a reddish-brown oil identified by NMR as the monosulfenylated product; evaporation of $Et_2O$ extract 1 afforded 300 mg of a mixture of mono- and disulfenylated product; evaporation of CHCl₃ extract afforded 900 mg of a mixture of monosulfenylated product and starting material in a ratio of 1:10.

Further basification of the original bicarbonate solution with 2.5N NaOH solution and extraction with CHCl₃ gave 2.5 g of unreacted amidine upon evaporation of the CHCl₃ extracts.

Dissolution of the monosulfenylated amidine product in 5 ml of absolute EtOH, acidification with EtOH/HCl and dilution with Et₂O afforded 3.3 g (22.9%) of the hydrochloride salt as a colorless, amorphous solid; m.p. 176°–178°.

Anal. Calc'd for $C_{14}H_{19}ClN_2S$: C, 59.45; H, 6.77; Cl, 12.53; N, 9.90; S, 11.33. Found: C, 59.54; H, 6.73; Cl, 13.08; N, 9.89; S, 11.07.

Example 11

Preparation of
2,3,5,6,7,8-Hexahydro-2-phenyl-8-phenylthioimidazo[1,2-a]pyridine sulfate (1:1) salt 2,3,5,6,7,8-Hexahydro-2-phenylimidazo[1,2-a]pyridine was reacted with 2 equivalents of n-BuLi and 1 equivalent of diphenyl disulfide according to the general procedure A above and afforded the free base as an oil in 91.2% yield. Treatment of the free base with EtOH/H₂SO₄ followed by Et₂O afforded the monosulfate salt as an amorphous powder (47.8%); m.p. 170°–175°.

Anal. Calc'd for $C_{19}H_{22}N_2O_4S_2$ C, 56.13; H, 5.45; N, 6.89; O, 15.74; S, 15.77. Found: C, 55.94; H, 5.50; N, 6.77; O, 15.99; S, 15.81.

Example 12

Preparation of
2,3,5,6,7,8-Hexahydro-2-phenyl-8-p-tolylthioimidazo[1,2-a]pyridine sulfate (1:1) salt 2,3,5,6,7,8-Hexahydro-2-phenylimidazo[1,2-a]pyridine was reacted with 2 equivalents of n-BuLi and 1 equivalent of p-tolyldisulfide according to the general procedure A above and afforded the free base an an oil in 90.6% yield. Treatment of the free base with EtOH/H₂SO₄ followed by Et₂ O afforded the monosulfate salt as a colorless, amorphous powder (22.8%); m.p. 154°–156°.

Anal. Calc'd for $C_{20}H_{24}N_2O_4S_2$: C, 56.00; H, 5.92; N, 6.47; O, 17.07; S, 15.27. Found: C, 56.03; H, 5.85; N, 6.53; O, 16.65; S, 14.96.

Example 13

Preparation of
2,3,5,6,7,8-Hexahydro-2-phenyl-8-p-chlorophenylthioimidazo[1,2-a]pyridine sulfate (1:1) salt 2,3,5,6,7,8-Hexahydro-2-phenylimidazo[1,2-a]pyridine was reacted with 2 equivalents of n-BuLi and 1 equivalent of bis(p-chlorophenyl)disulfide according to the general procedure A above and afforded the free base as an oil in 90.1% yield. Treatment of the free base with EtOH/H₂SO₄ followed by Et₂O afforded the monosulfate salt as a colorless, amorphous powder (22.7%); m.p. 135°–139°.

Anal. Calc'd for $C_{19}H_{21}Cl_1N_2O_4S_2$: C, 51.75; H, 4.80; Cl, 8.03; N, 6.35; O, 14.51; S, 14.54. Found: C, 51.82; H, 4.95; Cl, 7.91; N, 6.17; O, 15.28; S, 14.57.

Example 14

Preparation of
2,3,5,6,7,8-Hexahydro-2-phenyl-8-benzylthioimidazo[1,2-a]pyridine fumarate (1:1) salt 2,3,5,6,7,8-Hexahydro-2-phenylimidazo[1,2-a]pyridine was reacted with 2 equivalents of n-BuLi and 1 equivalent of benzyl disulfide according to the general procedure A above and afforded the free base as an oil in 56.5% yield. Treatment of the free base in n-propanol with 1 equivalent of fumaric acid followed by Et₂O afforded the fumarate salt as a colorless, amorphous powder (32.5%); m.p. 124°–129°.

Anal. Calc'd for $C_{24}H_{26}N_2O_4S$: C, 65.73; H, 5.97; N, 6.38; O, 14.59; S, 7.31. Found: C, 65.83; H, 6.20; N, 6.63; O, 14.92; S, 7.00.

Example 15

Preparation of
2,3,5,6,7,8-Hexahydro-2-phenyl-8-p-methoxybenzylthioimidazo[1,2-a]pyridine fumarate (1:1) salt 2,3,5,6,7,8-Hexahydro-2-phenylimidazo[1,2-a]pyridine was reacted with 2 equivalents of n-BuLi and 1 equivalent of p-methoxybenzyl disulfide according to the general procedure A above and afforded the free base as an oil in 52.7% yield. Treatment of the free base in n-propanol with 1 equivalent of fumaric acid followed by Et₂O afforded the fumarate salt as an off-white, amorphous solid (39.7%); m.p. 147°–149°.

Anal. Calc'd for $C_{25}H_{28}N_2O_5S$: C, 64.08; H, 6.02; N, 5.97; O, 17.07; S, 6.84. Found: C, 63.58; H, 6.22; N, 5.98; O, 17.01; S, 6.81.

Example 16

Preparation of
2,3,5,6,7,8-Hexahydro-2-phenyl-8,8-di(methylthio)imidazo[1,2-a]pyridine hydrochloride 2,3,5,6,7,8-Hexahydro-2-phenylimidazo[1,2-a]pyridine was reacted with 2 equivalents of n-BuLi and 2 equivalents of dimethyl disulfide according to general procedure B and afforded the free base as a solid in 90.2% yield; m.p. 87°–89°. Treatment of the free base with EtOH/HCl followed by ether yielded the hydrochloride salt as a colorless amorphous powder in 42.6% yield; m.p. 185°–188°.

Anal. Calc'd for $C_{15}H_{21}ClN_2S_2$: C, 54.77; H, 6.43; Cl, 10.77; N, 8.51; S, 19.49. Found: C, 54.90; H, 6.42; Cl, 10.85; N, 8.54; S, 19.21.

Example 17

Preparation of
2,3,5,6,7,8-Hexahydro-2-phenyl-8,8-di(phenylthio)imidazo[1,2-a]pyridine fumarate 2,3,5,6,7,8-Hexahydro-2-phenylimidazo[1,2-a]pyridine was reacted with 2 equivalents of n-BuLi and 2 equivalents of diphenyl disulfide according to the general procedure B and afforded the free base as an oil in 81.9% yield. Treatment of the free base in n-propanol with an equivalent of fumaric acid followed by ether afforded the fumarate salt as an off-white amorphous solid (52%); m.p. 157°–159°.

Anal. Calc'd for $C_{29}H_{28}N_2O_4S_2$: C, 65.39; H, 5.29; N, 5.25; O, 12.01; S, 12.03. Found: C, 65.13; H, 5.21; N, 5.21; O, 12.46; S, 11.89.

Example 18

Preparation of 2,3,5,6,7,8-Hexahydro-2-phenyl-8-i-propylthioimidazo[1,2-a]pyridine sulfate 2,3,5,6,7,8-Hexahydro-2-phenylimidazo[1,2-a]pyridine was reacted with 2 equivalents of n-BuLi and 1 equivalent of isopropyldisulfide according to the general procedure A above and afforded the free base as a solid in 52.1% yield. Treatment of the free base with EtOH/H$_2$SO$_4$ followed by Et$_2$O afforded the monosulfate salt as a light tan amorphous powder (20.2%); m.p. 116°–119°.

Anal. Calc'd for C$_{16}$H$_{24}$N$_2$S$_2$O$_4$: C, 51.59; H, 6.49; N, 7.52; S, 17.21; O, 17.18. Found: C, 51.27; H, 6.52; N, 7.47; S, 17.10; O, 17.10.

Example 19

Preparation of 2,3,5,6,7,8-Hexahydro-2-phenyl-8-methylthioimidazo[1,2-a]pyridine fumarate (1:1) salt 2,3,5,6,7,8-Hexahydro-2-phenylimidazo[1,2-a]pyridine was reacted with 2 equivalents of n-BuLi and 1 equivalent of dimethyldisulfide according to the general procedure A above and afforded the free base as a reddish-brown oil. Treatment of the free base in n-propanol with 1 equivalent of fumaric acid followed by Et$_2$O afforded the fumarate salt as an off-white, amorphous solid (53.1%); m.p. 160°–161°.

Anal. Calc'd for C$_{18}$H$_{22}$N$_2$O$_4$S: C, 59.64; H, 6.11; N, 7.72; O, 17.65; S, 8.84. Found: C, 59.60; H, 6.23; N, 7.57; O, 17.69; S, 8.80.

EXAMPLE 20

Preparation of 2,3,5,6,7,8-Hexahydro-2-phenyl-8-(2,6-dichlorophenylthio)imidazo[1,2-a]pyridine hydrochloride 2,3,5,6,7,8-Hexahydro-2-phenylimidazo[1,2-a]pyridine was reacted with 2 equivalents of n-BuLi and 1 equivalent of 2,6-dichlorophenyldisulfide according to the general procedure A above and afforded the free base as a colorless oil in 94.6% yield. Treatment of the free base with EtOH/HCl followed by Et$_2$O afforded the monohydrochloride salt as a colorless amorphous powder (23.7%); m.p. 193°–196°.

Anal. Calc'd for C$_{19}$H$_{19}$Cl$_3$N$_2$S: C, 55.15; H, 4.62; Cl, 25.70; N, 6.76; S, 7.74. Found: C, 54.97; H, 4.79; Cl, 24.78; M, 6.92; S, 8.02.

EXAMPLE 21

Preparation of 2,3,5,6,7,8-Hexahydro-3-phenyl-8-phenylthioimidazo[1,2-a]pyridine sulfate 2,3,5,6,7,8-Hexahydro-3-phenylimidazo[1,2-a]pyridine was reacted with 2 equivalents of n-BuLi and 1 equivalent of diphenyldisulfide according to the general procedure A above and afforded the free base as a reddish oil in 95.2% yield. Treatment of an ethanol solution of the free base with EtOH/H$_2$SO$_4$ followed by Et$_2$O afforded the sulfate salt as an off-white powder (35.4%); mp 118°–120°.

Example 22

Preparation of cis-2,3-Diphenyl-2,3,5,6,7,8-Hexahydro-8-phenylthioimidazo[1,2-a]pyridine cis-2,3-Diphenyl-2,3,5,6,7,8-hexahydroimidazo[1,2-a]pyridine was allowed to react with 2 equivalents of n-BuLi and 1 equivalent of diphenyldisulfide according to the general procedure A and afforded the free base as an oil in 68% yield.

Example 23

Preparation of 2,3,5,6,7,8-Hexahydro-B 2-phenyl-8,8-dimethoxyimidazo[1,2-a]pyridine hydrochloride To a solution of 2,3,5,6,7,8-hexahydro-2-phenyl-8-phenylthioimidazo[1,2-a]pyridine (30 gm, 0.1 mol) dissolved in 740 ml of MeOH was added Chloramine-T(89 gm, 0.3 mol) in 740 ml of MeOH and the solution was heated at reflux under N$_2$ for 16 hrs. The solution was then allowed to cool to room temperature and the solvent was evaporated off at reduced pressure. The oily residue was taken up in CHCl$_3$, washed with 2.5N NaOH, dried (Na$_2$SO$_4$) and filtered. The filtrate was extracted with dilute HCl, the acidic extracts combined, basified with aqueous NaHCO$_3$ solution and extracted with 10% MeOH/CHCl$_3$. The organic extracts were combined, dried, and evaporated to afford 20 gm (81.3%) of the dimethyl ketal as a light brown oil. Treatment of an ethanol solution of the free base with EtOH/HCl followed by Et$_2$O gave 12.5 gm (44.4%) of the hydrochloride salt as a colorless amorphous powder; mp 186°–188°.

Anal. Cal'd for C$_{15}$H$_{21}$ClN$_2$O$_2$: C 60.70; H, 71.3; Cl 11.95; N, 9.44. Found: C, 60.54; H, 71.4; Cl, 11.90; N, 9.34.

EXAMPLE 24

Preparation of 2,3,5,6,7,8-Hexahydro-2-phenyl-8,8-diethoxyimidazo[1,2-a]pyridine sulfate Reaction of 2,3,5,6,7,8-hexahydro-2-phenyl-8-phenylthiomidazo[1,2-a]pyridine with Chloramine-T as in the above example but using EtOH in place of MeOH afforded the diethoxy ketal as a dark oil. Treatment of an ethanol solution of the free base with EtOH/H$_2$SO$_4$ followed by Et$_2$O yielded the sulfate salt as a colorless amorphous powder; mp 142°–144°.

Anal. Calc'd for C$_{17}$H$_{26}$N$_2$O$_6$S: C, 52.83; H, 6.78; N, 7.25; S, 8.30. Found: C, 52.45; H, 6.77; N, 7.23; S, 8.61.

Example 25

Preparation of 2,5,6,7-Tetrahydro-2-phenyl-7,7-dimethoxy-3H-pyrrolo[1,2-a]imidazole sulfate To a methanol solution (135 ml) of 2,5,6,7-tetrahydro-2-phenyl-7,7-diphenylthio-3H-pyrrolo[1,2-a]imidazole (5.35 g) under N$_2$ was added, all at once, Chloramine-T (15.2 g) suspended in MeOH (135 ml) and the bright yellow solution was heated at reflux for 16 hours. The solution was then allowed to cool to room temperature and the solvent was evaporated off at reduced pressure. The oily residue was taken up in CHCl$_3$, washed with 2.5N NaOH, dried (Na$_2$SO$_4$) and filtered. The filtrate was extracted with dilute HCl. The acidic extracts were combined, basified with aqueous NaHCO$_3$ solution and extracted with 10% MeOH/CHCl₃. The organic extracts were combined, dried, and evaporated to afford 3.0 gm (91.6%) of the dimethyl ketal as a viscous oil. Treatment of an ethanol solution of the free base with EtOH/H₂SO₄ followed by Et₂O gave the sulfate salt as an amorphous powder (33.9%); mp 146°–148°.

Anal. Calc'd for $C_{14}H_{20}N_2O_6S$: C, 49.40; H, 6.16; N, 7.92; S, 9.44. Found: C, 48.49; H, 5.95; N, 7.88; S, 9.44.

Example 26

Preparation of 2,3,5,6,7,8-Hexahydro-3-phenyl-8,8-dimethoxy imidazo[1,2-a]pyridine hydrochloride To a solution of 2,3,5,6,7,8-hexahydro-3-phenyl-8-phenylthioimidazo[1,2-a]pyridine (13.7 g, 0.046 mol) dissolved in 350 ml of MeOH was added Chloramine-T (39.7 g, 0.14 mol) in 350 ml of MeOH and the solution was heated at reflux under N₂ for 16 hrs. The solution was allowed to cool to room temperature and the solvent was evaporated off at reduced pressure. The oily residue was taken up in CHCl₃, washed with 2.5N NaOH, dried (Na₂SO₄) and filtered. The filtrate was extracted with dilute HCl, the acidic extracts combined, basified with aqueous NaHCO₃ solution and extracted with 10% MeOH/CHCl₃. The organic extracts were combined, dried, and evaporated to afford 7.2 g (60.2%) of the dimethyl ketal as a brown oil. Treatment of an ethanol solution of the free base with EtOH/HCl followed by Et₂O afforded 3.5 g (25.7%) of the hydrochloride salt as a colorless amorphous powder; mp 183°–185°.

Anal. Calc'd for $C_{15}H_{21}ClN_2O_2$: C, 60.70; H, 71.3; Cl, 11.95; N 9.44. Found: C, 60.38; H, 7.18; Cl, 12.14; N, 9.30.

Example 27

Preparation of cis-2,3-Diphenyl-2,3,5,6,7,8-hexahydro-8,8-dimethoxyimidazo[1,2-a]pyridine sulfate Treatment of cis-2,3-diphenyl-2,3,5,6,7,8-hexahydro-8-phenylthioimidazo[1,2-a]pyridine with Chloramine-T and MeOH as described in Example 26 afforded the dimethyl ketal as an orange oil. Treatment of an ethanol solution of the free base with EtOH/H₂SO₄ followed by Et₂O gave the sulfate salt as an off-white powder; mp 139°–140°.

Example 28

Preparation of 2,3,5,6,7,8-Hexahydro-2-phenylsulfinylimidazo[1,2-a]pyridine sulfate To 9.65 g (0.032 mol) of 2,3,5,6,7,8-hexahydro-2-phenyl-8-phenylthioimidazo[1,2-a]pyridine dissolved in 500 ml of CH₂Cl₂ and cooled in an ice bath to 0° was added portionwise 7.1 g of m-chloroperbenzoic acid. After 3 hrs. at 0°, the solution was washed with aqueous NaHCO₃ solution, dried and evaporated. The residual semi-solid was dissolved in EtOH, treated with EtOH/H₂SO₄ followed by Et₂O yielding the sulfoxide (41%) as a colorless amorphous powder; mp 121°–123°.

Anal. Calc'd for $C_{19}H_{22}N_2O_5S_2$: C, 54.01; H, 5.25; N, 6.63; S, 15.18. Found: C, 53.84; H, 5.39; N, 6.53; S, 14.69.

Example 29

Preparation of 2,3,5,6,7,8-Hexahydro-2-phenyl-8-phenylsulfonylimidazo[1,2-a]pyridine sulfate To 3.0 g (9 mmoles) of 2,3,5,6,7,8-hexahydro-2-phenyl-8-phenylthioimidazo[1,2-a]pyridine dissolved in 50 ml of MeOH and cooled in an ice bath to 0° was added a solution of potassium hydrogen persulfate (16.6 g) in 50 ml of H₂O. After the addition, the mixture was allowed to warm to room temperature and stir for 4 hours. Water (100 ml) was then added and the mixture was extracted with CHCl₃ (3×50 ml). The CHCl₃ extracts were combined, dried (Na₂SO₄) and evaporated to afford the sulfone as a yellowish oil in 92% yield. Treatment of an ethanol solution of the free base with EtOH/H₂SO₄ gave 1.5 g (38.1%) of the sulfate salt as a colorless amorphous solid; mp 211°–213°.

Anal. Calc'd d for $C_{19}H_{22}N_2O_6S_2$: C, 52.04; H, 5.06; N, 6.38; S, 14.62. Found: C, 51.60; H, 5.19; N, 6.37; S, 14.74.

Example 30

Preparation of 5,6,7,8-Tetrahydro-2-phenyl-8-phenylthioimidazo[1,2-a]pyridine sulfate 5,6,7,8-Tetrahydro-2-phenylimidazo[1,2-a]pyridine was allowed to react with 2 equivalents of n-BuLi and 1 equivalent of diphenyl disulfide according to the general procedure A and afforded the monosulfenylated free base as an oil in 65% yield. Treatment of an ethanol solution of the free base with EtOH/H₂SO₄ gave the sulfate salt as a colorless amorphous solid (35.2%); mp 214°–217°.

Anal. Calc'd for $C_{19}H_{20}N_2O_4S_2$: C, 56.42; H, 4.99; N, 6.93; S, 15.85. Found: C, 56.44; H, 5.23; N, 6.70; S, 15.60.

Example 31

Preparation of 2,3,5,6,7,8-Hexahydro-3-phenyl-imidazo[1,2-a]pyridine-By The Aziridine Method To 0.5 g (4.1 mol) of 2-phenylaziridine dissolved in 15 ml of MeOH was added 1.0 g (3.9 mmol) of 2-methylthio-3,4,5,6-tetrahydropyridinium iodide and the resulting yellow reaction mixture was heated at reflux under N₂ for 2 hours. The reaction mixture was then allowed to cool to RT, the solvent evaporated off, and the residual oil taken up in CH₂Cl₂. The CH₂Cl₂ solution was washed with N NaOH, dried and evaporated to afford 0.9 g (100%) of the 3-phenylamidine derivative as a colorless oil; nmr and tlc were identical with material prepared by the method of Mohrle (Z. Naturforsch, 31b, 99–105; 1976).

Example 32

Preparation of cis-2,3-Diphenyl-2,3,5,6,7,8-hexahydroimidazo[1,2-a]pyridine-Aziridine Method Treatment of cis-2,3-diphenylaziridine with 2-methylthio-3,4,5,6-tetrahydropyridinium iodide as in Example 31 afforded the cis-2,3-diphenylamidine derivative as a colorless solid; mp 115°–117°.

Anal. Calc'd for $C_{19}H_{20}N_2$: C, 82.57; H, 7.29; N, 10.14. Found: C, 82.13; H, 7.25; N, 10.10.

Example 33

Preparation of
5,6,7,8-Tetrahydro-2-phenyl-8,8-diphenylthio imidazo[1,2-a]pyridine 5,6,7,8-Tetrahydro-2-phenylimidazo[1,2-a]pyridine was reacted with 2-equivalents of n-BuLi and 2 equivalents of diphenyldisulfide according to the general procedure B above and afforded the free base as an oil. Crystallization from ethanol gave the free base as off-white crystals (52.9%); mp 129°–131°.

Anal. Calc'd for $C_{25}H_{23}N_2S_2 \cdot \frac{1}{2}H_2O$: C, 70.89; H, 5.47; N, 6.61; S, 15.14. Found: C, 71.40; H, 5.49; N, 6.39; S, 14.28.

Example 34

Preparation of
2,3,5,6,7,8-Hexahydro-8,8-dimethoxy-4-methyl-2-phenylimidazo[1,2-a]pyridinium iodide To 3.5 g of 2,3,5,6,7,8-hexahydro-8,8-dimethoxy-2-phenylimidazo[1,2-a]pyridine dissolved in 100 ml of acetone was added in rapid drops with stirring 1.25 ml (excess) methyl iodide and the yellow solution was let stand undisturbed for 16 hours. The solid precipitate which had deposited was filtered off, washed well with cold acetone and air-dried; yield of colorless needles 4.1 g (75.0%), mp 176°–178°.

Anal. Calc'd for $C_{16}H_{23}N_2O_2I$: C, 47.77; H, 5.76; N, 6.96; O, 7.95; I, 31.53. Found: I, 31.22.

Example 35—Chemotaxis Assay

In this assay, done according to the methods of R. Synderman et al., *Infection & Immunity*, 11, p. 488–492 (1975) and M. S. Meltzer et al., *J. Natl. Cancer Inst.*, 54, p. 795–799 (1975), the ability of a drug substance to influence the movement of cells responding to a stimulus induced by some foreign substance or injury is determined. The results are reported in Table 35. This in vitro assay utilizes a chemoattractant, derived from a component of the immunological system known as complement, to induce murine macrophage cells to migrate toward it. The effect of a drug substance on such movements can be measured by counting the cells. Inflammation is a result of massive cell migration to the injured site and, thus, a compound exhibits anti-inflammatory activity by inhibiting cell migration. For example, the compound of Example 1 inhibits migration by 68.2% at $10^{-10}$ molar concentration and is thus an immunosuppressant. Conversely, macrophages can destroy tumors and, thus, compounds exhibit potential anti-cancer activity by stimulating migration of these cells. For example, the compound of Example 15 stimulates migration by 35.6% at $10^{-8}$ molar concentration and is thus immunoenhancing.

TABLE 35

| Compound of Example No: | Percent Inhibition (−) or Enhancement (+) at Dose of: | | | | | |
|---|---|---|---|---|---|---|
| | $10^{-5}$m | $10^{-7}$m | $10^{-8}$m | $10^{-9}$m | $10^{-10}$m | $10^{-11}$m |
| 1 | −25.4 | −8.8 | −17.5 | −29.7 | −68.2 | −36.8 |
| 3 | −94.9 | −64.5 | −43.0 | −29.2 | — | — |
| 10 | −94.1 | −94.4 | −88.4 | −91.7 | −97.4 | −97.3 |
| 14 | −29.1 | −51.0 | −51.0 | −50.7 | −10.2 | −44.5 |
| 15 | +2.6 | +30.1 | +35.6 | +31.8 | +33.8 | −1.2 |

Example 36—Kennedy Plaque Assay

In this assay, in which the in vitro model used was the Kennedy modification of the Jerne (or plaque) technique (J. C. Kennedy et al, *Immunol.*, 20, p. 253 (1971)), the animal's humoral immune system is depressed artificially by the known immunosuppressant drug, 6-mercaptopurine (6-MP), and then the ability of a drug to either suppress it further or restore it towards normal is evaluated. The results are reported in Table 36. The change in the number of plaques, which is a direct correlate of the change in the number of antibody secreting cells in the spleen, is used to measure this effect. For example, the compound of Example 11 results in greater than 100% restoration of the number of plaques and thus causes an immunoenhancement of the humoral system. In contrast, the compound of Example 28 results in about 24% further suppression of the number of plaques and thus behaves as an immunosuppressant.

TABLE 36

| Kennedy Plaque Assay | |
|---|---|
| Treatment with 60 mg/Kg of 6MP plus 6.25 mg/Kg (i.p.) of compound of example No. | Percent Restoration(+) or Suppression (−) (%) |
| 1 | +72 |
| 2 | +29 |
| 3 | +108 |
| 7 | −49 |
| 8[1] | −36[2] |
| 10 | +55 |
| 11 | +125 |
| 12 | +50 |
| 13 | +103 |
| 15 | +54 |
| 16 | −25 |
| 17[1] | −37[2] |
| 18 | +97 |
| 20 | −49 |
| 23 | +64 |
| 28 | −24 |
| 33 | +25 |

[1]without 6-MP treatment
[2]percent change from control (i.e., without 6-MP)

Example 37—Anti-inflammatory Assay

The anti-inflammatory properties of various compounds of this invention were determined by carrageenan-induced paw edemas of test rats. Male, Sprague-Dawley rats (Blue Spruce Farm) were ordered at 125–140 g, housed for one week, and allowed food and water ad libitum. At the time of the experiments, only rats weighing 160–200 g were used.

All compounds were dissolved or suspended in a 0.5% water solution of Methocel and orally administered to groups of six rats each. Control rats received Methocel only. Two hours later (unless otherwise stated), paw edema was induced by subcutaneous injection into the plantar surface of the right hind paw of 0.1 ml of a 1.0% homogenized suspension of carrageenan.

Immediately, the volume of the paw was measured by immersing it in mercury to above the lateral mateolus. The mercury in a glass cylinder 25 mm in diameter and 60 mm deep was connected at the bottom on the cylinder by a column of water to a Statham transducer (model P23BB), range 0–5 cm of mercury pressure. The volume was recorded electronically on a Beckman recorder, R511. Three hours later, the inflamed paw volume was measured again, and the change in volume was recorded for each group. The percent inhibition of edema was calculated using the control group paw volume as 100% edema, i.e., as (the change in edema in the control group less the change in edema in the test group) times 100 divided by the change in edema in the control group. The results are reported in Table 37.

TABLE 37

Anti-inflammatory Assay
Effect on Carrageenan Induced Edema

| Example No. | Dose (p.o.) mg/Kg | Percent Inhibition (%) |
|---|---|---|
| 17 | 50 | 38.6 |
| 18 | 50 | 40.4 |
| 20 | 100 | 33.3;39.6 |
| 23 | 50 | −3.2 |
| 23[1] | 50 | 34.5,49.5 |
| 23[2] | 50 | 32.1 |

[1]16 hrs. pre-dosed
[2]20 hrs. pre-dosed

Example 38—Antiviral Assay—Hepatitis In Mice

Female mice weighing approximately 21-24 grams were inoculated with 0.1 ml of a mouse liver suspension containing mouse hepatitis virus, which liver suspension is at a dilution of $10^{-5.5}$. Starting twenty-four hours post-virus inoculation, the animals were intraperitoneally ("i.p.") or orally administered the test compound(s) once daily for 3 days. On day 4, one third to one half of each group of mice were sacrificed and their liver removed for examination. Each liver was scored and assigned a number from 0 (normal liver) to 4 (extreme discoloration). The mean liver score per group was computed. The number of animals surviving until termination of the study (day 21) was also recorded. The results are reported in Table 38. Anti-hepatitis activity is evidenced by increased survivor numbers and improved liver scores.

TABLE 38

Antiviral Activity Against Hepatitis in Mice

| Example No. | Dose (i.p.) mg/Kg | Percent Survival % | Mean Liver Score |
|---|---|---|---|
| control | — | 5 | 2.6 |
| 16 | 6.25 | 60 | 1.5 |
| | 12.5 | 90 | 2.0 |
| control | — | 5 | 2.6 |
| 23 | 6.25 | 40 | 1.7 |
| | 12.5 | 70 | 1.0 |
| | 25.0 | 50 | 1.3 |
| control | — | 5 | 2.6 |
| 11 | 6.25 | 10 | 2.0 |
| | 12.5 | 40 | 1.8 |
| | 25.0 | 40 | 1.8 |
| control | — | 6 | 3.4 |
| 25 | 12.5 | 0 | 2.6 |

TABLE 38-continued

Antiviral Activity Against Hepatitis in Mice

| Example No. | Dose (i.p.) mg/Kg | Percent Survival % | Mean Liver Score |
|---|---|---|---|
| | 25 | 0 | 1.1 |
| | 50 | 0 | 1.2 |
| control | — | 6 | 3.4 |
| 26 | 12.5 | 0 | 2.7 |
| | 25 | 0 | 2.3 |

The amidine compounds of this invention may be used in the form of pharmaceutical preparations which contain the compound in association with a compatible pharmaceutical carrier. The preparations may be made up for oral, topical, parenteral, ophthalmic, nasal or rectal administration, preferably oral. The dosage form may be a solution, suspension, tablet, capsule or other suitable formulation.

It will be apparent to those skilled in the art that many modifications and changes may be made in the invention described above without departing from the scope and spirit of the invention.

What is claimed is:

1. A process for preparing the compound selected from the group consisting of (a) a 2-phenyl, 3-phenyl or 2,3-diphenyl-2,5,6,7-tetrahydro-3H-pyrrolo[1,2-a]imidazole which is disubstituted at the 7-position with —OR$_1$, (b) a 2-phenyl, 3-phenyl or 2,3-diphenyl-2,3,5,6,7,8-hexahydroimidazo[1,2-a]pyridine which is disubstituted at the 8-position with OR$_1$, and (c) a pharmaceutically acceptable salt of (a) or (b), wherein R$_1$ is hydrogen, lower alkyl, phenyl, benzyl, or phenyl or benzyl substituted by lower alkyl, amino, lower alkylamino, nitro, halogen, hydroxy or lower alkoxy; the 2,3-position of said compound has a single or a double bond; the phenyl groups at the 2 and/or 3 positions are unsubstituted or substituted with lower alkyl, amino, lower alkylamino, nitro, hydroxy, lower alkoxy or halogen; and, in the case where one of the 2 or 3 positions is substituted by a phenyl or substituted phenyl, then the other of said 2 and 3 positions may be substituted by a lower alkyl group;

which process comprises contacting the corresponding amidine compound, wherein the 7-position of the imidazole and the 8-position of the pyridine are mono- with —SR$_1$ rather than —OR$_1$, with an excess of a positive halogenating agent in alcohol and recovering from the resultant reaction mixture the desired ether derivative.

2. A process for preparing 2,3,5,6,7,8-hexahydro-2-phenyl-8,8-dimethoxyimidazo[1,2-a]pyridine which comprises contacting 2,3,5,6,7,8-hexahydro-2-phenyl-8-phenylthioimidazo[1,2-a]pyridine with excess chloramine-T in methanol and recovering from the resultant reaction mixture the desired compound.

* * * * *